United States Patent

Griss et al.

[11] 4,010,279
[45] Mar. 1, 1977

[54] BIPHENYLOXY DERIVATIVES AND ANTIHYPERLIPIDEMIC USE

[75] Inventors: Gerhart Griss; Wolfgang Grell; Rudolf Hurnaus, all of Biberach, Riss; Robert Sauter, Laupheim; Bernhard Eisele, Biberach, Riss; Nikolaus Kaubisch, Biberach, Riss; Matyas Leitold, Biberach, Riss, all of Germany

[73] Assignee: Boehringer Ingelheim GmbH, Ingelheim am Rhein, Germany

[22] Filed: Dec. 23, 1975

[21] Appl. No.: 643,700

[30] Foreign Application Priority Data

Jan. 9, 1975    Germany .......................... 2500692
Oct. 25, 1975   Germany .......................... 2547872

[52] U.S. Cl. .................. 424/309; 260/295 AM; 260/471 R; 260/501.11; 260/519; 260/557 R; 260/558 D; 260/558 P; 260/559 R; 260/559 D; 260/559 S; 260/562 P; 424/263; 424/319

[51] Int. Cl.² ............... A61K 31/24; C07C 103/84

[58] Field of Search ................. 260/471 R; 424/309

[56] References Cited

UNITED STATES PATENTS 3,781,328  12/1973  Witte et al. ............... 260/471 R
3,914,286  10/1975  Mieville ..................... 424/309

*Primary Examiner*—Richard L. Raymond
*Attorney, Agent, or Firm*—Hammond & Littell

[57] ABSTRACT

Compounds of the formula

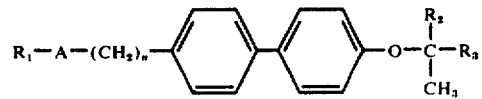

wherein
$R_1$ is straight or branched alkyl of 1 to 6 carbon atoms, cycloalkyl of 3 to 6 carbon atoms, phenylalkyl, phenylalkenyl, pyridyl or

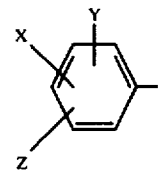

where X, Y and Z are each hydrogen, halogen, alkyl of 1 to 3 carbon atoms or alkoxy of 1 to 3 carbon atoms,
$R_2$ is hydrogen or alkyl of 1 to 4 carbon atoms,
$R_3$ is hydroxymethyl, carboxyl, alkoxycarbonyl of 2 to 7 carbon atoms or cycloalkoxycarbonyl or 4 to 8 carbon atoms,
A is —CO—NH— or —NH—CO—, and
$n$ is 1, 2 or 3, and, when $R_3$ is carboxyl, non-toxic salts thereof formed with an inorganic or organic base; the compounds as well as the salts are useful as antihyperlipidemics.

7 Claims, No Drawings

BIPHENYLOXY DERIVATIVES AND ANTIHYPERLIPIDEMIC USE

This invention relates to novel biphenyloxy derivatives, as well as to methods of preparing these compounds.

THE PRIOR ART

It is known that various alkyl phenoxy-propionates have antihyperlipidermic properties.

For instance, British Pat. No. 860,303 discloses that ethyl 2-(p-chloro-phenoxy)-2-methyl-propionate has antihypercholesteremic properties.

German Offenlegungsschrift No. 2,149,070 discloses that ethyl 2-methyl-2-{4-[β-(2-methoxy-5-chlorobenzamido)-ethyl]-phenoxy}-propionate exhibits similar properties.

And British Pat. No. 1,121,722 discloses that methyl 2-[4-(p-chloro-phenyl)-phenoxy]-2-methyl-propionate has antihyperlipidemic properties.

THE INVENTION

More particularly, the present invention relates to a novel class of biphenyloxy derivatives represented by the formula

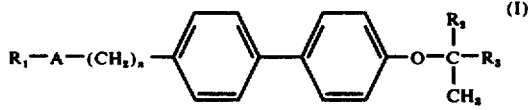

wherein
$R_1$ is straight or branched alkyl of 1 to 6 carbon atoms, cycloalkyl of 3 to 6 carbon atoms, phenylalkyl, phenylaldenyl, pyridyl or

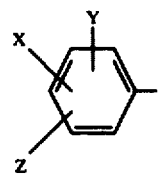

where X, Y and Z are each hydrogen, halogen, alkyl of 1 to 3 carbon atoms or alkoxy of 1 to 3 carbon atoms, $R_2$ is hydrogen or alkyl of 1 to 4 carbon atoms, $R_3$ is hydroxymethyl, carboxyl, alkoxycarbonyl of 2 to 7 carbon atoms or cycloalkoxycarbonyl of 4 to 8 carbon atoms, A is —CO—NH— or —NH—CO—, and n is 1, 2 or 3, and, when $R_3$ is carboxyl, non-toxic salts thereof formed with an inorganic or organic base.

Particularly preferred embodiments of the variants for substituents $R_1$, $R_2$ and $R_3$ are the following:

$R_1$ — Methyl, propyl, pentyl, hexyl, phenyl, benzyl, phenethyl, tolyl, fluorophenyl, chlorophenyl, bromophenyl, 2-methoxy-5-chloro-phenyl, dimethoxy-phenyl, trimethoxy-phenyl or phenyl-ethenyl;

$R_2$ — Hydrogen or methyl; and $R_3$ — Carboxyl, methoxycarbonyl, ethoxycarbonyl, propoxycarbonyl, isopropoxycarbonyl, butoxycarbonyl or hexyloxycarbonyl.

The compounds embraced by formula I may be prepared by the following methods:

Method A

By reacting a hydroxy-biphenylyl derivative of the formula

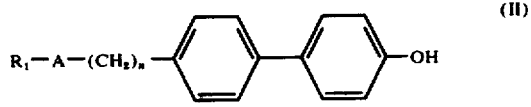

wherein $R_1$, A and n have the same meanings as in formula I with a compound of the formula

wherein $R_2$ and $R_3$ have the same meanings as in formula I and X is halogen

The reaction is advantageously carried out in the presence of a solvent, such as methyl ethyl ketone, dimethylformamide or glycol dimethyl ether, and preferably in the presence of a base, such as potassium carbonate or sodium hydride, at temperatures between 0° and 200° C, but preferably at the boiling point of the particular solvent which is used. The reaction may also be carried in the absence of a solvent, the reactants being in the molten state.

Method B

By reacting a diazonium salt of the formula

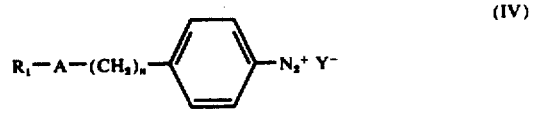

wherein
$R_1$, A and n have the same meanings as in formula I and
Y is the anion of an inorganic acid, such as the chloride anion, with a phenoxy derivative of the formula

wherein
$R_2$ and $R_3$ have the same meanings as in formula I.

The reaction is preferably carried out with a diazonium salt which is formed in situ from a corresponding aniline and sodium nitrite in the presence of an acid such as hydrochloric acid; and in the presence of a solvent, such as water, water/methanol or water/dioxane, advantageously at temperatures between 0 and 50° C, but preferably at room temperature.

If method A or B yields a compound of the formula I wherein $R_3$ is an esterified carboxyl group, this compound may be converted into the corresponding free carboxyl compound by hydrolysis, or into the corresponding hydroxymethyl compound by reduction with a complex metal hydride.

The hydrolysis is advantageously carried out in the presence of a solvent, such as water/dioxane, water/ethanol or water/methyl ethyl ketone, and preferably in the presence of a base, such as sodium hydroxide or potassium hydroxide and at temperatures up to the boiling point of the particular solvent which is used; the reduction is carried out in the presence of a solvent, such as ether, tetrahydrofuran or dioxane, with a complex metal hydride, such as lithium aluminum hydride, at temperatures between 20° and 60° C.

Those compounds of the formula I wherein $R_3$ is free carboxyl may be converted into their salts with inorganic or organic bases. Examples of non-toxic, pharmacologically acceptable salts are those formed with sodium hydroxide, potassium hydroxide or cyclohexylamine. The starting compounds of the formula II are also new and may be prepared by reacting a compound of the formula

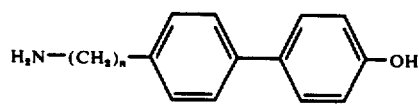

(VI)

wherein n has the meanings previously defined, with a compound of the formula $R_1 - CO - Z$     (VII)

wherein $R_1$ has the same meanings as in formula I and Z is hydroxyl or halogen; or by reacting a compound of the formula

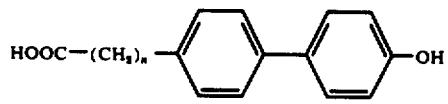

(VIII)

wherein n has the meanings previously defined, or a halide or anhydride thereof, with amine of the formula $R_1NH_2$, where $R_1$ has the same meanings as in formula I.

The reaction is advantageously carried out in the presence of a solvent, such as dioxane or water/dioxane, optionally in the presence of a base, such as potassium carbonate, sodium hydroxide, triethylamine or pyridine, and optionally in the presence of an acid-activating agent, such as cyclohexylcarbodiimide or thionyl chloride, at temperatures between 0° and 100° C.

The starting compounds of the formula VI may be prepared by the following methods:

a. Ether cleavage and hydrolysis of a compound of the formula

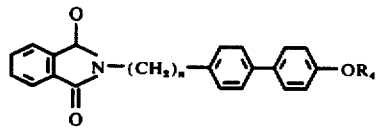

(IX)

wherein n has the meanings previously defined, and $R_4$ is lower alkyl of 1 to 3 carbon atoms, The reaction is preferably carried out in a medium suitable for ether cleavage and hydrolysis, such as hydrobromic acid or hydrobromic acid/glacial acetic acid at elevated temperatures, for example at the boiling point of the particular medium which is used.

b. Reduction of a compound of formula

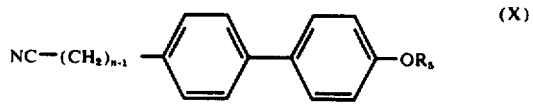

(X)

wherein n has the meanings previously defined, and $R_5$ is hydrogen or lower alkyl of 1 to 3 carbon atoms, and optional subsequent ether cleavage.

The reduction is preferably carried out in the presence of a solvent, such as methanol or methanol/ammonia, with nascent or catalytically activated hydrogen, for instance with hydrogen in the presence of Raney nickel at a pressure of 50 atmospheres and room temperature. The optional subsequent ether cleavage is advantageously carried out with hydrobromic acid/glacial acetic acid at the boiling point.

The starting compounds of the formula III are either disclosed in the literature, or may be prepared by conventional methods from the corresponding unhalogenated compounds by halogenation.

The starting compounds of the formula IV may be obtained from a corresponding aniline by diazotization with sodium nitrite, and the starting compounds of the formula V by reaction of phenol with a compound of the formula III in the presence of a base.

The following examples illustrate the present invention and will enable others skilled in the art to understand it more completely. It should be understood, however, that the invention is not limited solely to the particular examples given below. Preliminary note:

Some of the end products obtained in the following examples are oils which are very difficult to crystallize and, if at all, crystallize very slowly. Therefore, for the purpose of physical characterization, their M + H values were determined in a Finnigan mass spectrometer 3300 by chemical ionization, using isobutane as the reactant gas.

Preparation of starting compounds

EXAMPLE A

4-[2-Amino-ethyl]-4'-hydroxy biphenyl a. 77 ml (1080 millimols) of thionyl chloride were slowly added dropwise at 0° C to a suspension of 131 gm (540 millimols) of 2-[4-methoxy-biphenyl-(4')-yl]acetic acid (m.p. 184° C) in 540 ml of absolute ethanol. After heating the mixture for 30 minutes at its boiling point, the ethanol was distilled off in the rotary evaporator. The evaporation residue was dissolved in 2 liters of ether, the solution was washed free of acid with water, dried over sodium sulfate and, after distilling off the ether, the residue was recrystallized from a small quantity of ethanol 86 gm (59% of theory) of ethyl [4-methoxy-biphenyl-(4')-yl]-acetate m.p. 66° C, were obtained.

b. 44 gm (163 millimols) of this ester were reduced to 2-[4-methoxy-biphenyl-(4')-yl]-ethanol in 1.8 liters of ether with 3.4 gm (89 millimols) of lithium aluminum hydride. Yield: 33 gm (89% of theory), m.p.: 133° C.

c. 17.6 gm (77 millimols) of 2-[4-methoxy-biphenyl(4')-yl]-ethanol were added in small portions to 81 ml of thionyl chloride, and the mixtures was refluxed for 5 hours. After evaporation the residue was dissolved in chloroform and the solution was filtered through a silicagel column. After distilling off the chloroform, 11 gm (60% of theory) of 2-[4-methoxy-biphenyl-(4')-yl]ethyl chloride, m.p. <20° C, were obtained.

d. For the preparation of N-{2-[4-methoxy-biphenyl-(4')-yl]-ethyl}-phthalimide, 80 gm (326 millimols) of the above-obtained chloride were heated at 140° C in 1.4 liters of absolute dimethyl formamide with 61 gm (330 millimols) of phthalimide potassium for 9 hours. 73.5 gm (63% of theory) of the desired phthalimide, m.p. 189° C, were obtained.

e. The simultaneous ether cleavage and hydrolysis of the obtained phthalimide was effected by heating it in a mixture of aqueous 48% hydrobromic acid and glacial acetic acid (3:1) for 48 to 72 hours. The crude product was precipitated at a pH-value of 8.0 and recrystallized from a small quantity of absolute dimethylformamide. The 4-[2-aminoethyl]-4'-hydroxybiphenyl, m.p. >350° C, was obtained with a yield of 65 % of theory.

M + H = 214;
$M_{calc}$ = 213.27
Calculated: C-78.88%; H-7.10%; N-6.57%.
Found: C-78.30%; H-7.20%; N-6.83%.

EXAMPLE B

4-Aminomethyl-4'-hydroxy-biphenyl a. Ethyl [4-methoxy-biphenyl-(4')-yl]-acetate (see Example A) was converted into the corresponding hydrazide with hydrazine hydrate. Yield: 88% of theory; m.p. 210° C. b. 4-methoxy-4'-methoxycarbonylamidomethyl-biphenyl, m.p. 176° C, was obtained by Curtius decomposition of the hydrazide (see R. Robinson and W. M. Todd, J. Chem. Soc. 1939, 1744) with a yield of 65% of theory.

c. For ether cleavage and hydrolysis of the urethane, the 4-methoxy-4'-methoxycarbonylamidomethyl-biphenyl was heated in a mixture of aqueous 40% hydrobromic acid and glacial acetic acid (3:1 ) at its boiling point for 6 hours. After distilling off the solvents, the residue was dissolved in sodium hydroxide, and the crude product was precipitated by adjusting the pH of the solution to between 7 and 8, dried and recrystallized from a small quantity of absolute dimethylformamide. Yield: 69% of theory, m.p.: 165° C (decomp.).

EXAMPLE C

4-[3-Aminopropyl]-4'-hydroxy-biphenyl a. 4-[2-Cyanoethyl]-4'-methoxy-biphenyl was prepared from 4-[2-chloroethyl]-4'-methoxy-biphenyl (see Example A) by boiling with potassium cyanide in aqueous ethanol for 78 hours. Yield: 52% of theory; m.p. 105°–107° C.

b. 4-[3-Aminopropyl]-4'-methoxy-biphenyl-hydrochloride was prepared from 4-[2-cyanoethyl]-4'-methoxy-biphenyl by hydrogenation in methanolic ammonia at 50 atmospheres in the presence of Raney nickel as the catalyst. Yield: 80% of theory; m.p. 315°–317° C.

c. 4-[3-Aminopropyl]-4'-hydroxy-biphenyl as prepared from 4-[3-Amino-propyl]-4'-methoxy-biphenyl by cleavage with aqueous hydrobromic acid. Yield: 60% of theory; m.p. 300+ C.

EXAMPLE D

4-[2-(2-Methoxy-5-chloro-benzamido)-ethyl]-4'-hydroxy-biphenyl

A solution of 43 gm (20.1 millimols) of 4-[2-Aminoethyl]-4'-hydroxy-biphenyl in a mixture of 8.5 gm (21.3 millimols) of sodium hydroxide, 270 ml of water and 100 ml of dioxane, was acylated with 41.5 gm (20.1 millimols) of 2-methoxy-5-chloro-benzoyl chloride at 0° C. After stirring at room temperature for 2 hours, the mixture was extracted with chloroform, and the organic phase was dried over sodium sulfate. After distilling off the extracting agent, 72 gm (94% of theory) of a light yellow oil were obtained. This oil crystallized slowly and was uniform in the thin-layer chromatogram (silicagel; eluant: benzene/ethyl acetate = 7:2). After purification by column chromatography on silicagel with benzene/ethyl acetate as the eluant, the oil crystallized slowly. M.p. 169° C Calculated: C-69.20%; H-5.29%; N-3.68%.
Found: C-69.30%; H-5.31%; N-3.74%.

EXAMPLE E

4-[2-Methoxy-5-chloro-benzamido-methyl]-4'-hydroxy-biphenyl was prepared by acylation of 4-amino-methyl-4'-hydroxy-biphenyl (see Example B) in pyridine with an equimolar amount of 2-methoxy-5-chloro-benzoyl chloride at 50°–60° C. After precipitation with water, the crude product was purified on a silicagel column with benzene/ethyl acetate (7.5:2.5) as the eluant. Yield: 60% of theory; m.p. 144° C.

The acylation may also be effected with 2 equivalents of the acid chloride. The crude 4-[2-methoxy-5-chlorobenzamido-methyl]-4'-[2-methoxy-5-chloro-benzoyloxy]-biphenyl formed thereby was isolated and hydrolyzed with sodium hydroxide at room temperature. The further purification was effected as described above.

EXAMPLE F

4-[3-(2-Methoxy-5-chloro-benzamido)-propyl]-4'-hydroxy-biphenyl was prepared from 4-[3-aminopropyl]-4'-hydroxy-biphenyl by acylation with 2-methoxy-5-chloro-benzoyl chloride in dioxane/sodium hydroxide analogous to Example E. Yield 70% of theory; m.p. <20° C.

EXAMPLE G 4-(5-Chloro-2-methoxy-anilino-carbonyl-methyl)-4'-hydroxybiphenyl

A solution of 10 gm (44 millimols) of 4-hydroxy-4'-biphenyl-acetic acid (see W. H. Linnell and H. J. Smith, J. Chem. Soc. 1959,557) in a mixture of 33 ml of tetrahydrofuran and 162 ml of absolute dioxane were added at 0° C to a solution of 4.63 gm (29.4 millimols) of 2-methoxy-5-chloroaniline (m.p. 83°–85° C) in 40 ml of absolute dioxane, and the mixed solution was subsequently admixed with a solution of 9.1 gm (44 millimols) of N,N'-dicyclohexyl-carbodiimide in 20 ml of dioxane. After 20 hours of reaction time at 0° C, the dicyclohexylurea was filtered off and the solvent was distilled off. The residue was dissolved in 700 ml of chloroform, the solution was washed several times with 2N hydrochloric acid and water, dried over sodium sulfate, and the organic phase was evaporated in vacuo. The light brown, viscous crude product was purified on a silicagel column with toluene/acetic acid (4:1) as the eluant. Yield: 70% of theory; m.p. 165°–168° C.
 Calculated: C-68.50%; H-4.92%; N-3.80%.
 Found: C-68.50%; H-5.04%; N-3.92%.

EXAMPLE H

4-[2-(5-chloro-2-methoxy-anilino-carbonyl)-ethyl]-4′-hydroxybiphenyl

3-[4-Hydroxy-biphenyl-(4′)-yl]-propionic acid (m.p. 200°–204° C; prepared and described by W. H. Linnell and H. J. Smith, J. Chem. Soc. 1959, 557), was converted into 4-[2-(5-chloro-2-methoxy-anilino-carbonyl)-ethyl]-4′-hydroxy-biphenyl analogous to Example G. Yield: 70% of theory; m.p. 145°–150° C.
 Calculated: C-69.20%; H-5.23%; N-3.66%.
 Found: C-69.20%; H-5.46%; N-3.65%.

EXAMPLE I

4-[2-(2-Methoxy-benzamido)-ethyl]-4′-hydroxy-biphenyl

A solution of 9 gm (42 millimols) of 4-[2-aminoethyl]-4′-hydroxy-biphenyl in a solution of 1.72 gm (43 millimols) of sodium hydroxide in 100 ml of a mixture of water/dioxane (1:1) was acylated at 0° C with a solution of 13 gm (76 millimols) of 2-methoxybenzoyl chloride in 50 ml of dioxane, while maintaining the pH at 10 by periodic addition of sodium hydroxide. After all of the acid chloride had been added, the mixture was stirred at room temperature for 2 hours, and then the pH of the resulting suspension was adjusted to between 4 and 5 by addition of 2 N hydrochloric acid. The suspension was now extracted with chloroform. After extraction with a dilute sodium bicarbonate solution, the chloroform phase was dried with sodium sulfate, evaporated, and the residue was recrystallized from ethyl acetate. Yield: 8.7 gm (59% of theory); m.p. 118° C.
 Calculated: C-76.06%; H-6.09%; N-4.03%.
 Found: C-75.90%; H-6.21%; N-3.88%.

EXAMPLE J

4-[2-(3,4-Dimethoxy-benzamido)-ethyl]-4′-hydroxy-biphenyl was prepared analogous to Example I from 4-[2-amino-ethyl]-4′-hydroxy-biphenyl and 3,4-dimethoxybenzoyl chloride. Yield: 60% of theory; m.p. 170° C.

EXAMPLE K

4-[2-(2,4-Dimethoxy-benzamido)-ethyl]-4′-hydroxy-biphenyl was prepared analogous to Example I from 4-[2-amino-ethyl]-4′-hydroxy-biphenyl and 2,4-dimethoxybenzoyl chloride.
 Yield: 80% of theory; m.p. 190° C.
 Calculated: C-73.30%; H-6.14%; N-3.72%.
 Found: C-73.50%; H-6.36%; N-3.60%.

Preparation of end products of the formula I

EXAMPLE 1

Ethyl 2-Methyl-2- 4-[2-(2-methoxy-5-chloro-benzamido)-ethyl]-biphenyl-4′-ox -propionate by method A 5 gm (13millimols) of 4-[2-(2-methoxy-5-chlorobenzamido)-ethyl]-4′-hydroxy-biphenyl (see Example D) were converted into the sodium salt in 50 ml of absolute dimethylformamide with 700 mgm (16.6 millimols) of sodium hydride in the form of a 55% oil dispersion, and the salt was reacted with 3.24 gm (16.6 millimols) of ethyl 2-bromo-2-methylpropionate over a period of 16 hours at room temperature. After distilling off the dimethylformamide, the residue was dissolved in acetone, the solution was filtered and, after distilling off the acetone, the residue was purified on a silicagel column, with toluene/ethyl acetate (9:1) as the eluant. The fractions containing the pure product were combined, and the solvent was distilled off, yielding 3.6 gm (56% of theory) of a light yellow oil, m.p. 58°–60° C; which was identified to be the compound of the formula

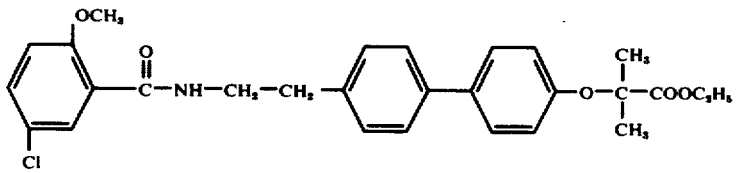

M + H = 496
$M_{calc}$ = 495.98
 Calculated: C-67.80%; H-6.10%; N-2.82%.
 Found: C-67.90%; H-6.31%; N-2.60%.

EXAMPLE 2

Methyl 2-Methyl-2-{4-[2-(2-methoxy-5-chloro-benzamido)-ethyl]biphenyl-4′-oxy}-propionate was prepared from 4-[2-(2-methoxy-5-chloro-benzamido)-ethyl]-4′-hydroxy-biphenyl and methyl 2-bromo-2-methyl-propionate analogous to Example 1. Yield: 19% of theory; m.p. <20° C.
 M + H = 482
 $M_{calc}$ = 481.96
 Calculated: C-67.46%; H-5.86%; N-2.9%.
 Found: C-67.6%; H-6.00%; N-2.7%.

EXAMPLE 3

Butyl 2-Methyl-{4-[2-(2:methoxy-5-chloro-benzamido)-ethyl]-biphenyl-4′-oxy}-propionate was prepared from 4-[2-(2-methoxy-5-chloro-benzamido-ethyl]-4′-hydroxy-biphenyl and butyl 2-bromo-2-methyl-propionate analogous to Example 1.
 Yield: 21% of theory; m.p. <20° C.
 M + H = 524
 $M_{calc}$ = 524.04.
 Calculated: C-68.8%; H-6.54%; N-2.68%.
 Found: C-68.2%; H-6.41%; N-2.48%.

EXAMPLE 4

Cyclohexyl 2-Methyl-2-{4-[2-(2-methoxy-5-chloro-benzamido)-ethyl]-biphenyl-4′-oxy}-propionate was prepared from 4-[2-(2methoxy-5-chloro-benzamido)- ethyl]-4'-hydroxy-biphenyl and cyclohexyl 2-bromo-2-methyl-propionate analogous to Example 1. Yield: 22% of theory; m.p. <20° C
M + H = 550
$M_{calc}$ = 550.08
Calculated: C-69.9%; H-6.6%; N-2.55%.
Found: C-69.8%; H-6.71%; N-2.52%.

EXAMPLE 5

Ethyl 2-{4-[2-(2-methoxy-5-chloro-benzamido)-ethyl]-biphenyl-4'-oxy}-propionate was prepared from 4-[2-(2-methoxy-5-chlorobenzamido)-ethyl]-4'-hydroxy-biphenyl and ethyl 2-bromo-propionate analogous to Example 1. Yield: 26% of theory; m.p. <20° C.
M + H = 482
$M_{calc}$ = 481.96
Calculated: C-67.4%; H-5,86%; N-2.9%.
Found: C-67.3%; H-5.98%; N-2.8%.

EXAMPLE 6

2-Methyl-2-{4-[2-(2-methoxy-5-chloro-benzamido)-ethyl]biphenyl-4'-oxy}-propionic acid was prepared by hydrolysis of the ester obtained as the end product in Example 1 with potassium hydroxide in water/dioxane (1:9) at room temperature. Yield: 75% of theory; m.p. 184° C.
M + H = 468
$M_{calc}$ = 467.96
Calculated: C-66.75%; H-5.60%; N-2.99%.
Found: C-66.60%; H-6.00%; N-2.85%.

EXAMPLE 7

2-{4-[2-(2-methoxy-5-chloro-benzamido)-ethyl]-biphenyl-4'-oxy}-propionic acid was prepared from the corresponding ethyl ester obtained as the end product in Example 5 by alkaline hydrolysis with potassium hydroxide in water/dioxane (1:9) at room temperature. Yield: 66% of theory; m.p. 145° C.
Calculated: C-66.25%; H-5.33%; N-3.04%.
Found: C-66.10%; H-5.46%; N:3.14%.

EXAMPLE 8

2-Methyl-2-{4-[2(2-methoxy-5-chloro-benzamido)-ethyl]-biphenyl-4'-oxy}-propanol 3.5 gm (7 millimols) of ethyl 2-methyl-2-{4-[2-(2-methoxy-5-chloro-benzamido)-ethyl]-biphenyl-4'-oxy}-propionate were reduced in 30 ml of absolute ether with 0.27 gm (7 millimols) of lithium aluminum hydride. After careful addition of 8 ml of water, the mixture was filtered, the filter cake was washed first with ether and then with chloroform, the ether phase and the chloroform phase were combined with the filrate and dried over sodium sulfate. After distilling off the solvents, the residual oil was crystallized from a small quantity of ether. Yield: 1.2 gm (38% of theory); m.p. 115° C.
M + H = 454
$M_{calc}$ = 453.9
Calculated: C-68.80%; H-6.22%; N-3.09%.
Found: C-68.80%; H-6.26%; N-3.15%.

EXAMPLE 9

Ethyl 2-Methyl-2-{4-[2-benzamido-ethyl]-biphenyl-4'-oxy}-propionate was prepared from 4-(2-benzamido-ethyl)-4'-hydroxybiphenyl and ethyl 2-bromo-2-methyl-propionate analogous to Example 1. Yield: 16% of theory; m.p. 100° C.
M + H = 432;
$M_{calc}$ = 431.54.

EXAMPLE 10

Ethyl 2-Methyl-2-{4-[2-(3-chloro-benzamido-ethyl]-biphenyl-4'-oxy}-propionate was prepared from 4-[2-(3-chloro-benzamido)-ethyl]-4'-hydroxy-biphenyl and ethyl 2-bromo-2-methyl-propionate analogous to Example 1. Yield: 32% of theory; m.p. 190° C.
M + H = 466;
$M_{calc}$ = 465.98.

EXAMPLE 11

Ethyl 2-Methyl-2-{4-[2-(4-chloro-benzamido)-ethyl]-biphenyl-4'-oxy}-propionate was prepared from 4-[2-(4-chloro-benzamido)-ethyl]-4'-hydroxy-biphenyl and ethyl 2-bromo-2-methyl-propionate analogous to Example 1. Yield: 21% of theory; m.p. 150° C.
M + H = 466;
$M_{calc}$ = 465.98.

EXAMPLE 12

Ethyl 2-Methyl-2-{4-[2-methoxy-benzamido)-ethyl]-biphenyl-4'-oxy}-propionate was prepared from 4-[2-(2-methoxy-benzamido)-ethyl]-4'-hydroxy-biphenyl and ethyl 2-bromo-2-methyl-propionate analogous to Example 1. Yield: 11% of theory; m.p. 74°–75° C.
M + H = 462;
$M_{calc}$ = 461.57;

EXAMPLE 13

Ethyl 2-Methyl-2-{4[2-(4-methyl-benzamido)-ethyl]-biphenyl-4'-oxy}-propionate was prepared from 4-[2-(4-methyl-benzamido)-ethyl]-4'-hydroxy-biphenyl and ethyl 2-bromo-2-methyl-propionate analogous to Example 1. Yield 17% of theory; m.p. 214° C.
M + H = 446.
$M_{calc}$ = 445.57.

EXAMPLE 14

Ethyl 2-Methyl-2-{4-[2-(4-fluoro-benzamido)-ethyl]-biphenyl-4'-oxy}-propionate was prepared from 4-[2-(4-fluoro-benzamido)ethyl]-4'-hydroxy-biphenyl and ethyl 2-bromo-2-methyl-propionate analogous to Example 1. Yield: 20% of theory; m.p. 135° C.

EXAMPLE 15

Ethyl 2-Methyl-2-{4-[2-(3-methyl-benzamido)-ethyl]-biphenyl-4'-oxy}-propionate was prepared from 4-[2-(3-methyl-benzamido)-ethyl]-4'-hydroxy-biphenyl and ethyl 2-bromo-2-methyl-propionate analogous to Example 1. Yield 19% of theory; m.p. <20° C.
M + H = 446;
$M_{calc}$ = 445.57.

EXAMPLE 16

Ethyl 2-Methyl-2-{4-[2-(2-methyl-benzamido)-ethyl]-biphenyl-4'-oxy}-propionate was prepared from 4-[2-(2-methyl-benzamido)-ethyl]-4'-hydroxy-biphenyl and ethyl 2-bromo-2-methyl-propionate analogous to Example 1. Yield: 20% of theory; m.p. <20° C
M + H = 446;
$M_{calc}$ = 445.52.

EXAMPLE 17

Ethyl 2-Methyl-2-{4-[2-(4-bromo-benzamido)-ethyl]-biphenyl-4'-oxy}-propionate was prepared from 4-[2-(4-bromo-benzamido)-ethyl]-4'-hydroxy-biphenyl and ethyl 2-bromo-2-methyl-propionate analogous to Example 1. Yield: 32% of theory; m.p. <20° C.

M + H = 511;
$M_{calc}$ = 510.41.

EXAMPLE 18

Ethyl 2-Methyl-2-{4-[2-(phenyl-acetamido)-ethyl]-biphenyl-4'-oxy}-propionate was prepared from 4-[2-(phenyl-acetamido)-ethyl]-4'-hydroxy-biphenyl and ethyl 2-bromo-2methyl-propionate analogous to Example 1. Yield: 26% of theory; m.p. <20° C.

M + H = 446;
$M_{calc}$ = 445.54.

EXAMPLE 19

Ethyl 2-Methyl-2-{4-[2-(cinnamoyl-amido)-ethyl]-biphenyl-4'-oxy}-propionate was prepared from 4-[2-(cinnamoyl-amido)-ethyl]-4'-hydroxy-biphenyl and ethyl 2-bromo-2-methyl-propionate analogous to Example 1. Yield: 16% of theory; m.p. 140° C.

Calculated: C-76.1%; H-6,82%; N-3.06%.
Found: C-76.7%; H-6.65%; N-3.39%.

EXAMPLE 20

Ethyl 2-Methyl-2-{4-[2-(cyclohexylcarbonyl-amido)-ethyl]-biphenyl-4'-oxy}-propionate was prepared from 4-[2-(cyclohexylcarbonyl-amido)-ethyl]-4'-hydroxy-biphenyl and ethyl 2-bromo-2-methyl-propionate analogous to Example 1. Yield: 24% of theory; m.p. <20° C.

M + H = 438;
$M_{calc}$ = 437.56.

EXAMPLE 21

Ethyl 2-Methyl-2-[4-(2-acetamido-ethyl)-biphenyl-4'-oxy]-propionate was prepared from 4-(2-acetamido-ethyl)-4'-hydroxybiphenyl and ethyl 2-bromo-2-methyl-propionate analogous to Example 1. Yield: 20% of theory; m.p. <20° C.

M + H = 370;
$M_{calc}$ = 369.45.

EXAMPLE 22

Ethyl 2-Methyl-2-[4-(2-caproylamido-ethyl)-biphenyl-4'-oxy]propionate was prepared from 4-(2-caproylamido-ethyl)-4'-hydroxy-biphenyl and ethyl 2-bromo-2-methyl-propionate analogous to Example 1. Yield: 24% of theory; m.p. 120° C.

M + H = 426;
$M_{calc}$ = 425.55.
Calculated: C-78.4%; H-8.20%; N-3.29%.
Found: C-73.7%; H-8.32%; N-3.47%.

EXAMPLE 23

Ethyl 2-Methyl-2-{4-[2-phenyl-propionylamido)ethyl]-biphenyl-4'-oxy}-propionate was prepared from 4-[2-(2-phenylpropionylamido)-ethyl]-4'-hydroxy-biphenyl and ethyl 2-bromo-2-methyl-propionate analogous to Example 1. Yield: 14% of theory; m.p. < 20° C.

M + H = 460;
$M_{calc}$ = 459.56.

EXAMPLE 24

Ethyl 2-Methyl-2-{4-[2-nicotinoylamido-ethyl]-biphenyl-4'-oxy}-propionate was prepared from 4-[2-nicotinoylamido-ethyl]-4'-hydroxy-biphenyl and ethyl 2-bromo-2-methyl-propionate analogous to Example 1. Yield: 8% of theory; m.p. < 20° C.

M + H = 433;
$M_{calc}$ = 432.5.

EXAMPLE 25

Ethyl 2-Methyl-2-{4-[2-methoxy-5-chloro-benzamido-methyl]-biphenyl-4'-oxy}-propionate by method A 2.7 gm (7.35 millimols) of 4-[2-methoxy-5-chlorobenzamido-methyl]-4'-hydroxy-biphenyl were refluxed in 30 ml of methyl ethyl ketone with 1.26 gm (9.2 millimols) of potassium carbonate for 1 to 2 hours, and then 2.23 gm (11 millimols) of ethyl 2-bromo-2-methyl-propionate were added dropwise. After three hours, another 0.63 gm (4.6 millimols) of potassium carbonate and 0.46 gm (2.2 millimols) of 2-bromo-2-methyl-propionate were added to complete the reaction, and the mixture was heated for 3 to 4 hours more. After cooling, filtering and distilling off the solvent, the residual crude product was purified by chromatography on a silicagel column with benzene/ethyl acetate (9:1) as the eluant. The evaluation of column chromatograph was carried out by thin-layer chromatography. The fractions containing the pure product were combined, and the solvent was distilled off, yielding 1.8 gm (51% of theory) of a slightly yellow oil. M.p. < 20° C.

M + H = 482;
$M_{calc}$ = 481.97.
Calculated: C-67.29%; H-5.86%; N-2.91%.
Found: C-67.50%; H-5.85%; N-2.49%.

EXAMPLE 26

2-Methyl-2-{4-(2-methoxy-5-chloro-benzamido-methyl)-biphenyl-4'-oxy}-propionic acid was prepared by alkaline hydrolysis of 2-methyl-2- 4-[2-methoxy-5-chloro-benzamido-methyl]-biphenyl-4'-oxy -propionate in 1 N potassium hydroxide and dioxane (1:5) at room temperature. Yield: 72% of theory; m.p. 104° C Calculated: C-66.16%; H-5.34%; N-3.09%.
Found: C-66.50%; H-5.31%; N-3.13%.

EXAMPLE 27

2-Methyl-2-{4-[(2-methoxy-5-chloro-benzamido)-methyl]-biphenyl-4'-oxy}-propanol 1.8 gm (3.74 millimols) of ethyl 2-methyl-2- 4-[(2-methoxy-5-chloro-benzamido)-methyl]-biphenyl-4'-oxy -propionate were reduced to the alcohol by heating in 50 ml of ether with 0.1 gm (3.8 millimols) of lithium aluminum hydride at the boiling point of the solvent for 15 minutes. After decomposition with water, drying of the ether phase over sodium sulfate, and distilling off the ether, the alcohol was purified on a silicagel column with benzene/ethyl acetate (6:4) as the eluant. Yield: 0.5 gm (30% of theory); m.p. 109° C.

Calculated: C-68.25%; H-5.96%; N-3.18%.
Found: C-68.10%; H-5.96%; H-3.05%.

EXAMPLE 28

Ethyl 2-methyl-2-{4-[3-(2-methoxy-5-chloro-benzamido)-propyl]-biphenyl-4-oxy}-propionate was prepared from 4-[3-(2-methoxy-5-chloro-benzamido)-propyl]-4'-hydroxy-biphenyl and ethyl 2-bromo-2-methyl-propionate analogous to Example 1. Yield: 15% of theory; m.p. < 20° C.

M + H = 510;
$M_{calc}$ = 510.01.

EXAMPLE 29

Ethyl 2-methyl-2-[4-(5-chloro-2-methoxy-anilinocarbonyl-methyl)-biphenyl-4'-oxy]-propionate by method A A 55% suspension of 2.57 gm (58.8 millimols) of sodium hydride in oil was washed free of oil with absolute ether, and the residual sodium hydride was suspended in 60 ml of absolute dimethylformamide. While stirring the resulting suspension at 20° C in an atmosphere of nitrogen, a solution of 10.8 gm (about 29.4 millimols) of raw 4-(5-chloro-2-methoxyanilinocarbonyl-methyl)-4'-hydroxy-biphenyl in 40 ml of dimethylformamide was added dropwise thereto. The resulting mixture was stirred on a bath at 80° C for 1½ hours more, and then 11.5 gm (58.8 millimols) of ethyl 2-bromo-2-methylpropionate were added and the mixture was stirred at 100° C for 3 hours. After evaporation in vacuo, water was added, and the mixture was extracted with ethyl acetate/ether (2:1). The organic extract was washed with water, dried over sodium sulfate, filtered and evaporated to dryness in vacuo. The dark brown, viscous evaporation residue was purified by chromatography on silicagel with toluene/ethyl acetate (4:1). The combined uniform fractions were evaporated and dried at 80° C/1 mm Hg, yielding 1.7 gm (12% of theory) of a bright red, viscous substance, m.p. < 20° C, which was identified to be the compound of the formula

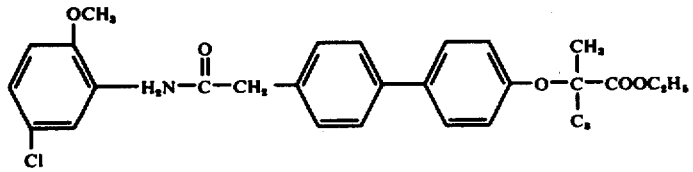

M + H = 482;
$M_{calc}$ = 481.9.
Calculated: C-67.25%; H-5.85%; N-2.91%.
Found: C-67.20%; H-5.98%; N-2.81%.

EXAMPLE 30

Ethyl 2-methyl-2-{4-[2-(5-chloro-biphenyl-methoxy-anailinocarbonyl)-ethyl]-biphenyl 4'-oxy}-propionate was prepared from 4-[2-(5-chloro-2-methoxy-anilino-carbonyl)-ethyl]-4'-hydroxy-biphenyl and ethyl 2-bromo-2-methyl-propionate analogous to Example 29. Yield: 17% of theory; m.p. < 20° C.

M + H = 496;
$M_{calc}$ = 495.98.
Calculated: C-67.60%; H-6.08% N-2.82%.
Found: C-67.40%; H-6.03%; N-2.96%.

EXAMPLE 31

Ethyl 2-methyl-2-{4-[2-(4-methoxy-benzamido)-ethyl]-biphenyl-4'-oxy}-propionate by method A 7.4 gm (21.2 millimols) of 4-[2-(4-methoxy-benzamido)-ethyl]-4'-hydroxy-biphenyl (see Example 1) were dissolved in 60 ml of absolute dimethyl formamide and converted into the sodium salt with 1.1 gm (about 25 millimols) of 55% sodium hydride suspension in oil, and the salt was reacted with 9.7 gm (51.5 millimols) of ethyl 2-bromo-2-methyl-propionate at room temperature over a period of 18 hours. After distilling off the dimethylformamide, the evaporation residue was dissolved in acetone, the solution was filtered, the acetone was distilled out of the filtrate, and the residue was purified on a silicagel column with toluene/ethyl acetate (4:1) as the eluant. Yield: 2 gm (20% of theory); m.p. 149°-150° C.

Calculated: C-72.90%; H-6.90%; N-3.10%.
Found: C-72.85%; H-6.72%; N-3.09%.

EXAMPLE 32

Ethyl 2-methyl-2-{4-[2-(3-methoxy-benzamido)-ethyl]-biphenyl-4'-oxy}-propionate was prepared from 4-[2-(3-methoxy-benzamido)-ethyl]-4'-hydroxy-biphenyl and ethyl 2-bromo-2-methylpropionate analogous to Example 31. Yield: 20% of theory; m.p. 70° C.

Calculated: C-72.90%; H-6.90%; N-3.10%.
Found: C-72.75%; H-6.71%; N-3.04%.

EXAMPLE 33

Ethyl 2-methyl-2-{4-[2-(3,4-dimethoxy-benzamido)-ethyl]-biphenyl-4'-oxy}-propionate was prepared from 4-[2-(3,4-dimethoxy-benzamido)-ethyl]-4'-hydroxy-biphenyl and ethyl 2-bromo-2-methyl-propionate analogous to Example 31. Yield: 22% of theory; m.p. 118° C.

M + H = 491;
$M_{calc}$ = 491.56.
Calculated: C-70.90% H-6.77%; N-2.85%.
Found: C-71.45%; H-7.06%; N-2.98%.

EXAMPLE 34

Ethyl 2-methyl-2-{4-[2-(3,5-dimethoxy-benzamido)-ethyl]-biphenyl-4'-oxy}-propionate was prepared from 4-[2-(3,5-dimethoxy-benzamido)-ethyl]-4'-hydroxy-biphenyl and ethyl 2-bromo-2-methyl-propionate analogous to Example 31. Yield: 20% of theory; m.p. 74° C.
M + H = 491;

$M_{calc} = 491.56$.
Calculated: C-70.90%; H-6.77%; N-2.85%.
Found: C-70.60%; H-6.53%; N-2.62%.

EXAMPLE 35

Ethyl 2-methyl-2-{4-[2-(2,3-dimethoxy-benzamido)-ethyl]-biphenyl-4'-oxy}-propionate was prepared from 4-[2-(2,3,-dimethoxy-benzamido)-ethyl]-4'-hydroxy-biphenyl and ethyl 2-bromo-2-methyl propionate analogous to Example 31. Yield: 27% of theory; m.p. < 20° C.
$M + H = 491$; $M_{calc} = 491.56$.
Calculated: C-70.90%; H-6.76%; N-2.85%.
Found: C-71.00%; H-6.78%; N-2.66%.

EXAMPLE 36

Ethyl 2-methyl-2-{4-[2-(2,4-dimethoxy-benzamido-ethyl-biphenyl-4'-oxy}-propionate was prepared from 4-[2-(2,4-dimethoxybenzamido)-ethyl]-4'-hydroxy-biphenyl and ethyl 2-bromo-2-methyl-propionate analogous to Example 31. Yield: 22% of theory; m.p. 92° C.
$M + H = 491$;
$M_{calc} = 491.56$.

EXAMPLE 37

Ethyl 2-methyl-2-{4-[2-(2,6-dimethoxy-benzamido)-ethyl]-biphenyl-4'-oxy}-propionate was prepared from 4-[2-(2,6-dimethoxy-benzamido)-ethyl]-4'-hydroxy-biphenyl and ethyl 2-bromo-2-methyl-propionate analogous to Example 31. Yield: 20% of theory; m.p. < 20° C.
$M + H = 491$;
$M_{calc} = 491.56$.

EXAMPLE 38

Ethyl-2-methyl-2-{4-[2-(3,4,5-trimethoxy-benzamido)-ethyl]-biphenyl-4'-oxy}-propionate was prepared from 4-[2-(3,4,5-trimethoxy-benazmido)-ethyl]-4'-hydroxy-biphenyl and ethyl 2-bromo-2-methyl-propionate analogous to Example 31. Yield: 6% of theory; m.p. < 20° C
$M + H = 521$;
$M_{calc} = 521.59$.

EXAMPLE 39

2-Methyl-2-{4-[2-(2-methoxy-benzamido)-ethyl]-biphenyl-4'-oxy}-propionic acid

4gm (8.6 millimols) of ethyl 2-methyl-2- 4-[2-(2-methoxy-benzamido)-ethyl]-biphenyl-4'-oxy -propionate were hydrolized at room temperature over a period of 12 hours with a solution of 1gm (17.2 millimols) of potassium hydroxide in 5 ml of water and 95 ml of methanol. After distilling off the methanol, 100 ml of water were added, and the mixture was extracted with ether. The pH of the aqueous phase was adjusted to between 1 and 2 with 2 N hydrochloric acid, and the acid mixture was extracted with chloroform. The combined chloroform extracts were dried over sodium sulfate and evaporated to dryness, and the residue was recrystallized from ether. Yield: 3.2 gm (86% of theory); m.p. 133° C.
Calculated: C-72.03%; H-6.27%; N-3.23%.
Found: C-71.80%; H-6.32% N-3.28%.

EXAMPLE 40

2-Methyl-2-{4-[2-(3-methoxy-benzamido)-ethyl]-biphenyl-4'-oxy}-propionic acid was prepared from the corresponding ethyl ester by alkaline hydrolysis analogous to Example 39. Yield: 80% of theory; m.p. 117° C.
Calculated: C-72.10%; H-6.28%; N-3.28%.
Found: C-71.90%; H-6.45%;N-3.37%.

Example 41

2-Methyl-2-{4-[2-(4-methoxy-benzamido)-ethyl[-biphenyl-4'-oxy}-propionic acid was prepared from the corresponding ethyl ester by alkaline hydrolysis analogous to Example 39. Yield: 82% of theory; m.p. 180°-183° C.
$M + H = 433$;
$M_{calc} = 433.49$.
Calculated: C-70.90%; H-6.28%; N-3.49%.
Found: C-71.10%; H-6.28%; N-3.28%.

EXAMPLE 42

2-Methyl-2-{4-[2-benzamido-ethyl]-biphenyl-4'-oxy}-propionic acid was prepared from the corresponding ethyl ester (m.p. 100° C) by alkaline hydrolysis analogous to Example 39. Yield: 82% of theory; m.p. 179° C.
Calculated: C-74.40%; H-6.25%; H-3.48%.
Found: C-74.40%; H-6.27%; N-3.43%.

EXAMPLE 43

2-Methyl-2-{4-[2-3,4-dimethoxy-benzamido)-ethyl]-biphenyl-4'-oxy}-propionic acid was prepared from the corresponding ethyl ester by alkaline hydrolysis analogous to Example 35. Yield: 80% of theory; m.p. 184° C.
$M + H = 463$;
$M_{calc} = 463.51$.

EXAMPLE 44

2-Methyl-2-{4-[2-(2,3-dimethoxy-benzamido)-ethyl]-biphenyl-4'-oxy}-propionic acid was prepared from the corresponding ethyl ester by alkaline hydrolysis analogous to Example 39. Yield: 83% of theory; m.p. 184° C.
$M + H = 463$;
$M_{calc} = 463.51$.

EXAMPLE 45

2-Methyl-2-{4-[2-nicotinoyl-amido-ethyl]-biphenyl-4'-oxy}-proionic acid was prepared from the corresponding ethyl ester (m.p. 98° C) by alkaline hydrolysis analogous to Example 39. Yield: 37% of theory; m.p. 179° C.
$M + H = 404$;
$M_{calc} = 404.45$.
Calculated: C-71.40%; H-5.97%; H-6.93%.
Found: C-71.50%; H-6.07%; N-6.75%.

EXAMPLE 46

2-Methyl-2-{4-[2-(2-methoxy-benzamido)-ethyl]-biphenyl-4'-oxy}-propionic acid by method A 0.5 gm (1.4 millimols) of 4-[2-(2-methoxy-benzamido)-ethyl]-4'-hydroxy-biphenyl were heated at 90°-130° C for 90 minutes with 0.025 gm of 2-bromo-2-methyl-propionic acid. The reaction product was isolated by chromatography on silicagel with chloroform/methanol (9:1) as the eluant. M.P. 133° C. $M + H = 433$;
$M_{calc} = 433.50$.

EXAMPLE 47

2-Methyl-2-{4-[2-(5-chloro-2-methoxy-benzamido)-ethyl]-biphenyl-4'oxy}-propionic acid was prepared from 4-[2-(5-chloro-2-methoxy-benzamido)-ethyl]-4'-hydroxy-biphenyl and 2-bromo-2-methyl-propionic acid analogous to Example 46. M.p. 145° C.

M + H = 468;
$M_{calc}$ = 467.96.

The compounds of the present invention, that is those embraced by formula I above and their non-toxic, pharmacologically acceptable salts, have useful pharmacodynamic properties. More particularly, the lower the cholesterol and triglyceride level in the blood of warm-blooded animals, such as rats, and are therefore useful as antihyperlipidemics.

The above pharmacological activity of the compounds of this invention, as well as their acute toxicities, were ascertained along with those of the three antihyperlipidemic compounds of the prior art by the standard test methods described below. Tables I and II show the results obtained for a few representative species of the genus, where A = ethyl 2-methyl-2-{4-[2-methoxy-5-chloro-benzamido)-ethyl]-biphenyl-4'-oxy}-propionate, B = 2-methyl-2-{4-[2-(2-methoxy-5-chloro-benzamido)-ethyl]-biphenyl-4'-oxy}-propionic acid, C = ethyl 2-methyl-2-{4-[2-(2-methoxy-benzamido)-ethyl]biphenyl-4'-oxy}-propionate, D = 2-methyl-2-{4-[2-(2-methoxy-benzamido)-ethyl]-biphenyl-4'-oxy}-propionic acid, E = ethyl 2-(4-chlorophenoxy)-2-methyl-propionate, F = methyl 2-[4-(4-chlorophenyl)-phenoxy]-2-methyl-propionate, and G = ethyl 2-methyl-2-{4-[2-(2-methoxy-5-chloro-benzamido)-ethyl]-phenoxy}-propionate.

1. Lipid lever lowering activity:

The test compound was administered twice by an esophageal tube at 20 hours' interval to male normolipemic rats having a body weight of 250–300 gm. When the test began, the animals were deprived of food, but water was freely acessible to them. 28 and 44 hours later the serum cholesterol- and triglyceride-levels were determined. The measurement of cholesterol and triglycerides was effected simultaneously, using an autoanalyzer; the percentage depression was calculated, compared with a control group treated with placebo.

The cholesterol-lowering activity of the test compound was observed after oral administration of one dose and after oral administration of various doses. From these data the dose leading to a 15% ($ED_{15}$) and a 20% ($ED_{20}$) depression of the cholesterol level in the serum was determined by regression analysis:

TABLE I

| Compound | Time After the beginning of the test in hours | Dose (mg/kg) | Cholesterol level lowering activity $ED_{15}$ mg/kg | $ED_{20}$ mg/kg |
|---|---|---|---|---|
| Invention: | | | | |
| A | 28 | 1 – 10 | 2.1 | 3.9 |
|   | 44 | 1 – 10 | 1.9 | 3.1 |
| B | 28 | 1 – 20 | – | 15.97 |
|   | 44 | 1 – 20 | – | 4.41 |
| C | 28 | 1 – 10 | – | 9.88 |
|   | 44 | 1 – 10 | – | 2.68 |
| D | 28 | 1 – 10 | – | 3.10 |
|   | 44 | 0.5 – 10 | – | 0.59 |
| Prior Art: | | | | |
| E | 28 | 25 – 100 | 15 | 22 |
|   | 44 | 25 – 100 | 25 | 32 |
| F | 28 | 1 – 10 | 6.9 | 11 |
|   | 44 | 1 – 10 | 4.4 | 5.6 |
| G | 28 | 1 – 25 | 3.6 | 5.0 |
|   | 44 | 1 – 30 | 3.6 | 5.0 |

2. Acute toxicity

The acute toxicity was determined on groups of 5 or 6 white mice each, after oral administration of the test compound at dosage levels of 2.5 g/kg, 5 g/kg and 10 g/kg (observation time 14 days).

TABLE II

| Compound | Toxicity ($LD_{50}$) |
|---|---|
| Invention: | |
| A | >10 g/kg (0 out of 5 animals died) |
| B | >10 g/kg (0 out of 5 animals died) |
| C | >10 g/kg (0 out of 5 animals died) |
| D | > 2.5 g/kg (1 out of 5 animals died) |
| Prior Art: | |
| E | 1.7 g/kg* |
| F | 5 g/kg (3 out of 5 animals died) |
| G | 2.5 g/kg (3 out of 6 animals died) |

*see Therapie 27, 385 (1972).

For pharmaceutical purposes the compounds according to the present invention are administered to warm-blooded animals perorally, parenterally or rectally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective antihyperlipidemic dosage unit of the compounds according to the present invention is from 0.08 to 1.67 mgm/kg body weight, preferably 0.08 to 0.5 mgm/kg body weight. The daily dose rate is 0.16 to 5.0 mgm/kg, preferably 0.25 to 1.5 mgm/kg.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 48

Suppositories

The suppository composition is compounded from the following ingredient:

| | |
|---|---|
| Ethyl 2-methyl-2-{4-[2-(2-methoxy-5-chloro-benzamido)-ethyl]-biphenyl-4-oxy}-propionate | 0.030 parts |
| Suppository base (e.g. cocoa butter) | 1.670 parts |
| Total | 1.700 parts |

Preparation

The milled propionate is homogeneously stirred into the suppository base which had previously been melted and cooled to 40° C. 1700 mgm portions of the resulting mixture are poured into cooled suppository molds and allowed to harden therein. Each suppository contains 30 mgm of the propionate and is a rectal dosage unit composition with effective antihyperliperdemic action.

EXAMPLE 49

Gelatin capsule

The capsule filler composition is compounded from the following ingredients:

| | | |
|---|---|---|
| Ethyl 2-methyl-2-{4-[2-(2-methoxy-5-chloro-benzamido)-ethyl]-biphenyl-4'-oxy}-propionate | | 5.0 parts |
| Corn starch dried | | 100.0 parts |
| Corn starch, powdered | | 93.0 parts |
| Magnesium stearate | | 2.0 parts |
| | Total | 200.0 parts |

Preparation

The ingredients are admixed with each other, the mixture is passed through a 0.75 mm mesh screen, and the screened composition is homogenized in a suitable mixer. 200 mgm portions of the resulting powder are filled with No. 3 hard gelatin capsules. Each capsule contains 5 mgm of the propionate and is an oral dosage unit composition with effective antihyperlipidemic action.

EXAMPLE 50

Tablets

The tablet composition is compounded from the following ingredients:

| | | |
|---|---|---|
| Ethyl 2-methyl-2-{4-[2-(2-methoxy-5-chloro-benzamido)-ethyl]-biphenyl-4''-oxy}-propionate | | 25.0 parts |
| Lactose | | 35.0 parts |
| Corn starch | | 15.0 parts |
| Polyvinylpyrrolidone | | 4.5 parts |
| Magnesium stearate | | 0.5 parts |
| | Total | 80.0 parts |

Preparation

The propionate, the lactose and the corn starch are intimately admixed with each other; the mixture is uniformly moistened with an aqueous solution of the polyvinylpyrrolidone, the moist mass is forced through a 1.5 mm mesh screen, and the resulting granulate is dried at 45° C in a drying chamber with circulating air and again passed through a 1.0 mm mesh screen. The dry granulate is admixed with the magnesium stearate, and the composition is compressed into 80 mgm tablets in a conventional tablet making machine. Each tablet contains 25 mgm of the propionate and is an oral dosage unit composition with effective antihyperlipidemic action.

EXAMPLE 51

Coated pills

The pill core composition is compounded from the same ingredients and in the same manner as the tablet composition of the preceding example, and the composition is compressed into 80 mgm pill cores. The cores are then coated with a thin shell consisting essentially of a mixture of talcum and sugar, and the coated pills are finally polished with beeswax. Each coated pill contains 25 mgm of the propionate and is an oral dosage unit composition with effective antihyperlipidemic action.

Analogous results are obtained when any one of the other compounds embraced by formula I or a non-toxic salt thereof is substituted for the particular propionate in Examples 48 through 51. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

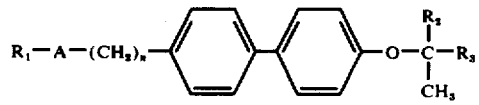

wherein
  $R_1$ is alkyl of 1 to 6 carbon atoms, cycloalkyl of 3 to 6 carbon atoms, phenylalkyl, phenylalkenyl or

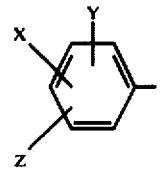

where X, Y and Z are each hydrogen, halogen, alkyl of 1 to 3 carbon atoms or alkoxy of 1 to 3 carbon atoms,
  $R_2$ is hydrogen or alkyl of 1 to 4 carbon atoms,
  $R_3$ is alkoxycarbonyl of 2 to 7 carbon atoms or cycloalkoxycarbonyl of 4 to 8 carbon atoms,
  A is —CO-NH— or —NH-Co—, and
  $n$ is 1, 2 or 3.

2. A compound of claim 1, which is of the formula

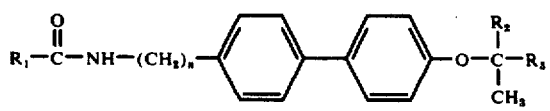

wherein
  $R_1$ is alkyl of 1 to 6 carbon atoms, cycloalkyl of 3 to 6 carbon atoms, phenylalkyl, phenylalkenyl or

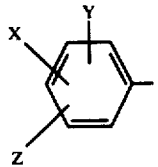

wherein X, Y and Z are each hydrogen, halogen, alkyl or 1 to 3 carbon atoms or alkoxy of 1 to 3 carbon atoms, $R_2$ is hydrogen or alkyl of 1 to 4 carbon atoms, $R_3$ is alkoxycarbonyl of 2 to 7 carbon atoms or cycloalkoxycarbonyl of 4 to 8 carbon atoms, and $n$ is 1, 2 or 3.

3. A compound of claim 2, which is of the formula

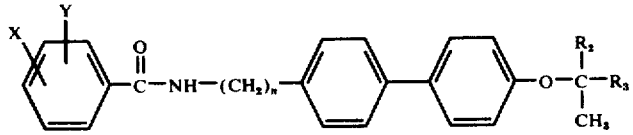

wherein $R_2$ is hydrogen or methyl, $R_3$ is carbalkoxy of 2 to 5 carbon atoms, X and Y are each hydrogen, fluorine, chlorine, bromine, methyl or mexthoxy, and $n$ is 1, 2 or 3.

4. The compound of claim 3 which is ethyl 2-methyl-2- 4-[2-(2-methoxy-5-chloro-benzamido)-ethyl]-biphenyl-4'-oxy -propionate.

5. The compound of claim 3 which is ethyl 2-methyl

6. An antihyperlipidemic pharmaceutical dosage unit composition consisting essentially of an inert pharmaceutical carrier and an effective antihyperlipidermic amount of a compound of claim 1.

7. The method of lowering the level of lipids in the blood of a warm-blooded animal in need of such treatment, which comprises perorally, parenterally or rectally admininstering to said animal an effective antihyperlipidemic amount of a compound of claim 1.

* * * * *